(12) United States Patent
LaFrancois et al.

(10) Patent No.: US 8,817,241 B2
(45) Date of Patent: *Aug. 26, 2014

(54) OIL IN WATER ANALYZER

(71) Applicant: Phillips 66 Company, Houston, TX (US)

(72) Inventors: Christopher J. LaFrancois, Bartlesville, OK (US); James F. Stewart, Bartlesville, OK (US); Gregory C. Allred, Bartlesville, OK (US); Marion Ash, Nanwalek, AK (US)

(73) Assignee: Phillips 66 Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/051,492

(22) Filed: Oct. 11, 2013

(65) Prior Publication Data

US 2014/0036255 A1    Feb. 6, 2014

Related U.S. Application Data

(63) Continuation of application No. 13/020,266, filed on Feb. 3, 2011, now Pat. No. 8,570,497.

(60) Provisional application No. 61/302,334, filed on Feb. 8, 2010.

(51) Int. Cl.
| | | |
|---|---|---|
| *G01N 33/28* | (2006.01) | |
| *G01J 3/00* | (2006.01) | |
| *G01N 33/18* | (2006.01) | |
| G01N 21/35 | (2014.01) | |
| G01N 21/33 | (2006.01) | |
| G01N 21/41 | (2006.01) | |
| G01N 21/64 | (2006.01) | |

(52) U.S. Cl.
CPC ............ *G01N 33/1833* (2013.01); *G01N 21/35* (2013.01); *G01N 21/33* (2013.01); *G01N 21/41* (2013.01); *G01N 21/64* (2013.01); *G01N 21/3577* (2013.01)
USPC ............................................. 356/70; 356/300

(58) Field of Classification Search
USPC ................. 356/70, 300, 302; 73/61.48, 61.69
See application file for complete search history.

(56) References Cited

U.S. PATENT DOCUMENTS

| | | | | |
|---|---|---|---|---|
| 4,103,162 | A * | 7/1978 | Iwamoto et al. | 250/343 |
| 4,207,450 | A * | 6/1980 | Mittleman | 250/343 |
| 4,352,983 | A * | 10/1982 | Silvus et al. | 250/227.25 |
| 4,624,133 | A * | 11/1986 | Iwashita | 73/61.43 |
| 4,647,371 | A * | 3/1987 | Schmitt et al. | 210/96.1 |
| 4,943,161 | A * | 7/1990 | Michaelis et al. | 356/437 |
| 5,186,817 | A * | 2/1993 | Paspek et al. | 208/188 |
| 2001/0003426 | A1* | 6/2001 | Matter et al. | 324/698 |

\* cited by examiner

*Primary Examiner* — Kara E Geisel
*Assistant Examiner* — Dominic J Bologna
(74) *Attorney, Agent, or Firm* — Phillips 66 Company

(57) ABSTRACT

An oil in water analyzer for measuring the concentration of hydrocarbons in an effluent stream. The oil in water analyzer has a valve system for acquiring a sample from an effluent stream. An extraction device is used for mixing a known volume of a solvent and the sample to produce a hydrocarbon/solvent mixture. A second valve is used for transporting the hydrocarbon/solvent mixture to a spectroscopic cell. It is at the spectroscopic cell where the concentration of hydrocarbons in the hydrocarbon/solvent mixture is evaluated.

2 Claims, 10 Drawing Sheets

STANDARD VALVE BODY

MODIFIED VALVE BODY

BORED TO ACCEPT WELD FITTING

WELD FITTING

FINISHED VALVE BODY

WELDED CONNECTION

OIL IN WATER ANALYZER

CROSS-REFERENCE TO RELATED APPLICATIONS

This application is a continuation application which claims the benefit and priority to U.S. patent application Ser. No. 13/020,266, filed Feb. 3, 2011, which claims the benefit and priority to U.S. Provisional Application Ser. No. 61/302,334, filed Feb. 8, 2010, which are both entitled "Oil in Water Analyzer", which are both hereby incorporated by reference in the entirety.

STATEMENT REGARDING FEDERALLY SPONSORED RESEARCH OR DEVELOPMENT

None

FIELD OF THE INVENTION

Oil in water analyzer for analyzing the quantity of oil in an effluent stream.

BACKGROUND OF THE INVENTION

The production of oil from underground reservoirs results in crude oil containing varying amounts of water generally in the form of a water-in-oil emulsion. It is general practice to dehydrate the crude oil by allowing it to stand but oftentimes the dehydration is enhanced by the addition of a demulsifier to break the emulsion facilitating physical separation of the crude oil from the water. Following this dehydration step, the crude oil is transported to the refinery where it may undergo an initial dewatering procedure and/or subjected to the process of desalting, i.e. the removal of salts from hydrocarbon crude oil, sometimes employing the action of an electrocoalescer.

Salts in hydrocarbon crude oil are generally dissolved in small droplets of water or brine dispersed throughout the crude. Sodium chloride is the primary salt followed by calcium chloride, magnesium chloride and the sulfates of these three metals. The total salt content ranges from substantially zero to several hundred pounds per thousand barrels of crude.

These brine droplets are generally prevented from coalescing and settling by a tough, elastic film at the surface of each droplet. This film is stabilized by natural emulsifiers found in the crude, solids, and solid hydrocarbons that concentrate at the droplet surface. A desalting chemical or demulsifier displaces these natural emulsifiers and solids and weakens the film so the droplets of brine can coalesce when they contact each other.

A new oil field will frequently produce crude with negligible water and salt. As production continues, the amount of water produced increases, raising the salt content of the crude. Additional salt contamination often occurs during tanker shipment. An empty tanker takes on sea water as ballast and often uses it to wash the tanks. To minimize pollution, the top, oily layer of ballast water and the washings are segregated in a slop compartment when the ballast water is discharged. Fresh crude is then loaded on top of this slop oil and water. The entire compartment is then offloaded at the refinery.

As earlier inferred, some brine can be removed by settling and water drawoff in the refinery's crude storage tanks. Some demulsifiers are very effective in increasing the rate and amount of settling as well as preventing sludge buildup and in cleaning tanks where sludge has already accumulated. Typically, the demulsifier formulation is injected into the turbulent crude flow as it fills the storage tank at a treat rate of from 10 to 500 ppm. The settled brine is drawn before the crude is charged to the pipestill.

To enhance the effectiveness of electrostatic desalter, desalting chemicals are used in combination with an imposed electric field. Desalting chemicals are usually a blend of surface active materials in hydrocarbon solvents. These materials are preferentially absorbed at the brine droplet surface, displacing the solids and natural emulsifiers. This greatly weakens the film around the droplets. The brine droplets can then coalesce with the wash water (thus diluting the brine) and with other droplets so their size becomes large enough to settle by gravity. Depending on its composition and solvent, the desalting chemical may also dissolve the film.

To overcome solids stabilization of an emulsion, a good demulsifier formulation will cause the oil-wet solids to become water-wet and settle into the water phase where they are removed with the effluent water. A surfactant can also be used alone or in combination with the demulsifier for this purpose. These chemicals work by attaching an oil-loving or solids-loving section of the molecule to an oil-wetted solid. A water-loving section then physically drags the solid into the water phase. These molecules can also agglomerate solids to speed their settling. Without chemical treatment, most oil-wet solids will stay in the oil phase even though their density is higher.

With the rising value of petroleum products, it becomes increasingly important that separator equipment utilized by the petroleum industry extract the maximum possible recovered petroleum products from oil and water emulsions and dispersions. These are main issues that currently affect the profitability and operating integrity related to oil carryover in effluent water streams from dewatering/desalting systems.

There exists a need to continuously monitor the oil carryover in effluent water streams to ensure that maximum profitability can be maintained.

SUMMARY OF THE INVENTION

An oil in water analyzer for measuring the concentration of hydrocarbons in an effluent stream. The oil in water analyzer has a valve system for acquiring a sample from an effluent stream. An extraction device is used for mixing a known volume of a solvent and the sample to produce a hydrocarbon/solvent mixture. A second valve is used for transporting the hydrocarbon/solvent mixture to a spectroscopic cell. It is at the spectroscopic cell where the concentration of hydrocarbons in the hydrocarbon/solvent mixture is evaluated.

An alternate embodiment provides a method for continuously altering the process based upon the concentration of hydrocarbon material in the sample. The method begins by producing an effluent stream. A sample is acquired from the effluent stream then transferred into an extraction device. A known volume of a water-immiscible solvent is injected into the extraction device. The sample and the water-immiscible solvent are then mixed in the extraction device. The hydrocarbon component of the sample is extracted into the water-immiscible solvent to produce a hydrocarbon/solvent mixture which is transported to a spectroscopic cell.

In yet another embodiment the oil in water analyzing method begins with producing an effluent stream from a dewatering/desalting operation. in this embodiment the effluent stream flows through a sample loop. From about 0.5 mL to about 50 mL of a sample of the effluent stream is trapped in the sample loop. This sample is they transferred to an extraction device with the assist of a pressurized gas. A known volume of toluene is injected into the extraction device. Air is then flowed through a venturi to create a pumping action to produce a hydrocarbon/solvent mixture from the sample. The hydrocarbon/solvent mixture is then transferred to a spectroscopic cell with a water assist. The hydrocarbon concentration of the hydrocarbon/solvent mixture is determined by spectroscopy techniques. The leftover hydrocarbon/solvent mixture and water are then transferred to a waste removal port with the assist of pressurized gas. An amount of toluene is injected into the system to solvent rinse the oil in water analyzer. In this method the operation of the dewatering/desalting operation is adjusted based upon the concentration of the hydrocarbon material in the sample.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

Figure 1:
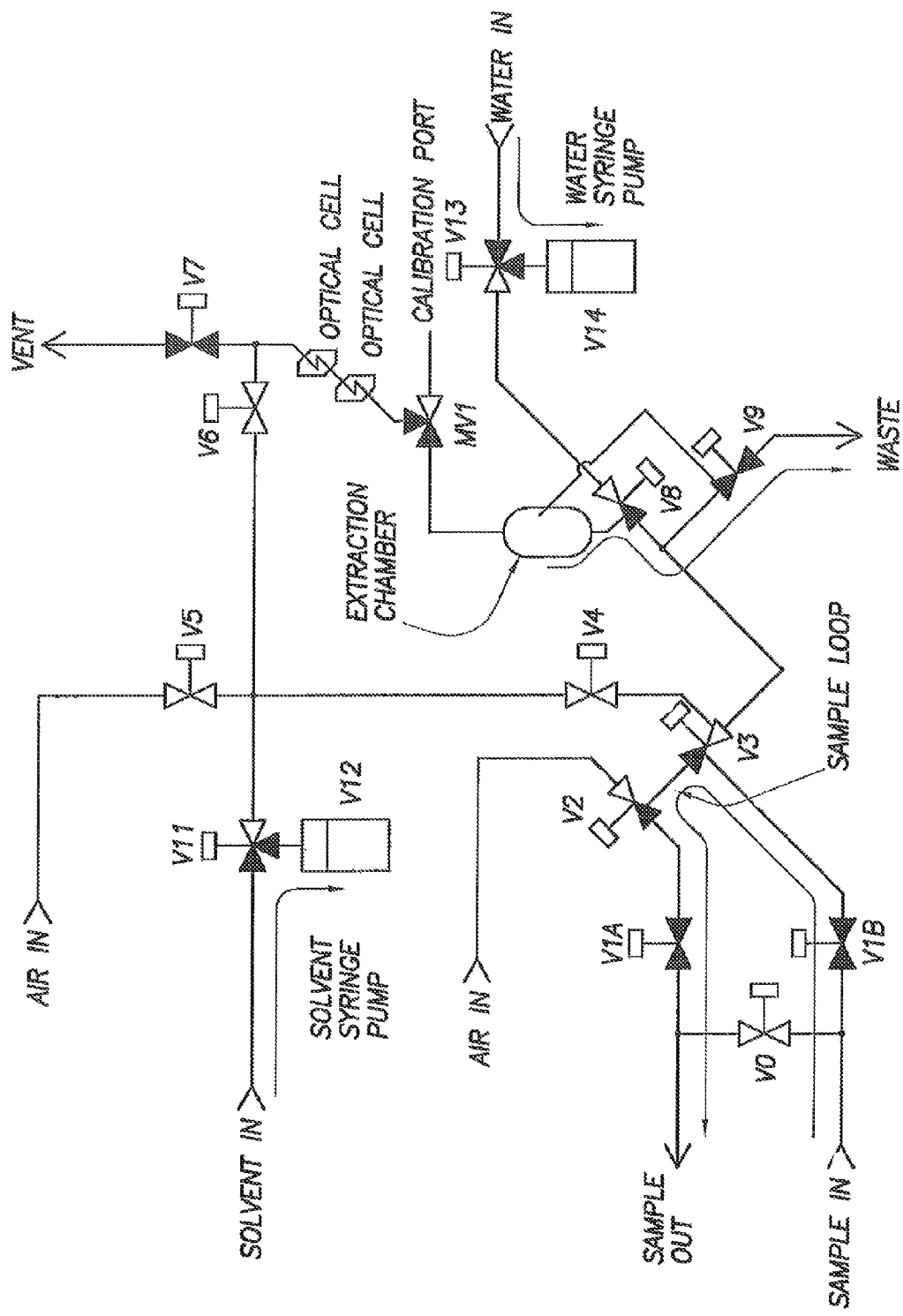
FIG. 1 depicts step 1 of how a sample is tested in the analyzer.

The present embodiment describes an oil in water analyzer. The oil in water analyzer has a valve system for acquiring a sample from an effluent stream. An extraction device is used for mixing a known volume of a solvent and the sample to produce a hydrocarbon/solvent mixture. A second valve is used for transporting the hydrocarbon/solvent mixture to a spectroscopic cell it is at the spectroscopic cell where the concentration of hydrocarbons in the hydrocarbon/solvent mixture is evaluated.

The valve system can be a single valve or an assortment of valves that are connected together in a manner to acquire the sample from the effluent stream.

The present embodiment additionally provides a method for continuously altering the process based upon the concentration of hydrocarbon material in the sample. The method begins by producing an effluent stream. A sample is acquired from the effluent stream then transferred into an extraction device. A known volume of a water immiscible solvent is injected into the extraction device. The sample and the water-immiscible solvent are mixed and the hydrocarbon component is extracted. The hydrocarbon/solvent mixture is then transferred to the spectroscopic cell via a water assist.

A water assist is a situation where water is flowed through a tube and used to push a sample, in this scenario a hydrocarbon/solvent mixture, from one area in the tube to another area.

In yet another embodiment the oil in water analyzing method begins with producing an effluent stream from a dewatering/desalting operation. In this embodiment the effluent stream flows through a sample loop. From about 0.5 mL to about 50 mL of a sample of the effluent stream is trapped in the sample loop. This sample is then transferred to an extraction device with the assist of a pressurized gas. A known volume of toluene is injected into the extraction device. Air is then flowed through a venturi to create a pumping action to produce a hydrocarbon/solvent mixture from the sample. The hydrocarbon/solvent mixture is then transferred to a spectroscopic cell with the water assist. The hydrocarbon concentration of the hydrocarbon/solvent mixture is determined by spectroscopy techniques. The leftover hydrocarbon/solvent mixture and water are then transferred to a waste removal port with the assist of pressurized gas. An amount of toluene is injected into the system to solvent rinse the oil in water analyzer. in this method the operation of the dewatering/desalting operation is adjusted based upon the concentration of the hydrocarbon material in the sample. This adjustment is necessary to maintain the operation of the dewatering/desalting unit within specified oil concentration limits.

The oil in water analyzer can be used for a variety of purposes such as waste water, food industry water, deoiling and other application. Preferably the oil in water analyzer is used in a dewatering/desalting operation.

In the dewatering/desalting of heavy (high specific gravity, high viscosity) crude oils, or lighter crude oils containing emulsion stabilizers in the form of clay, asphaltenes, paraffins and other solids, the virgin crude oils are subjected to mixing with wash water in one or two stages, usually in horizontal contacting dewatering/desalting vessels. When the recovery of every processable drop of oil is sought, it is particularly advantageous to continuously analyze the effluent stream containing the brine, the oil emulsion under-carry including the oil-wetted solids that remain in the oil phase, and the intermittent mud wash solids.

The oil in water analyzer has the capability to measure 10 to 50,000 ppm of crude oil in water when utilizing ultra violet spectroscopic detection. Other configurations implementing optional detectors (visible, infrared, and fluorescence spectroscopy as well as refractive index) will have varying capability and will be constructed to achieve application specific performance.

Figures

FIGS. 1-8 describe an embodiment of the present method. In FIG. 1 the effluent stream is directed through the sample loop via V1A and V1B. Toluene and water are loaded into their respective syringe pumps and residues from the previous samples are drained to waste.

Figure 2:
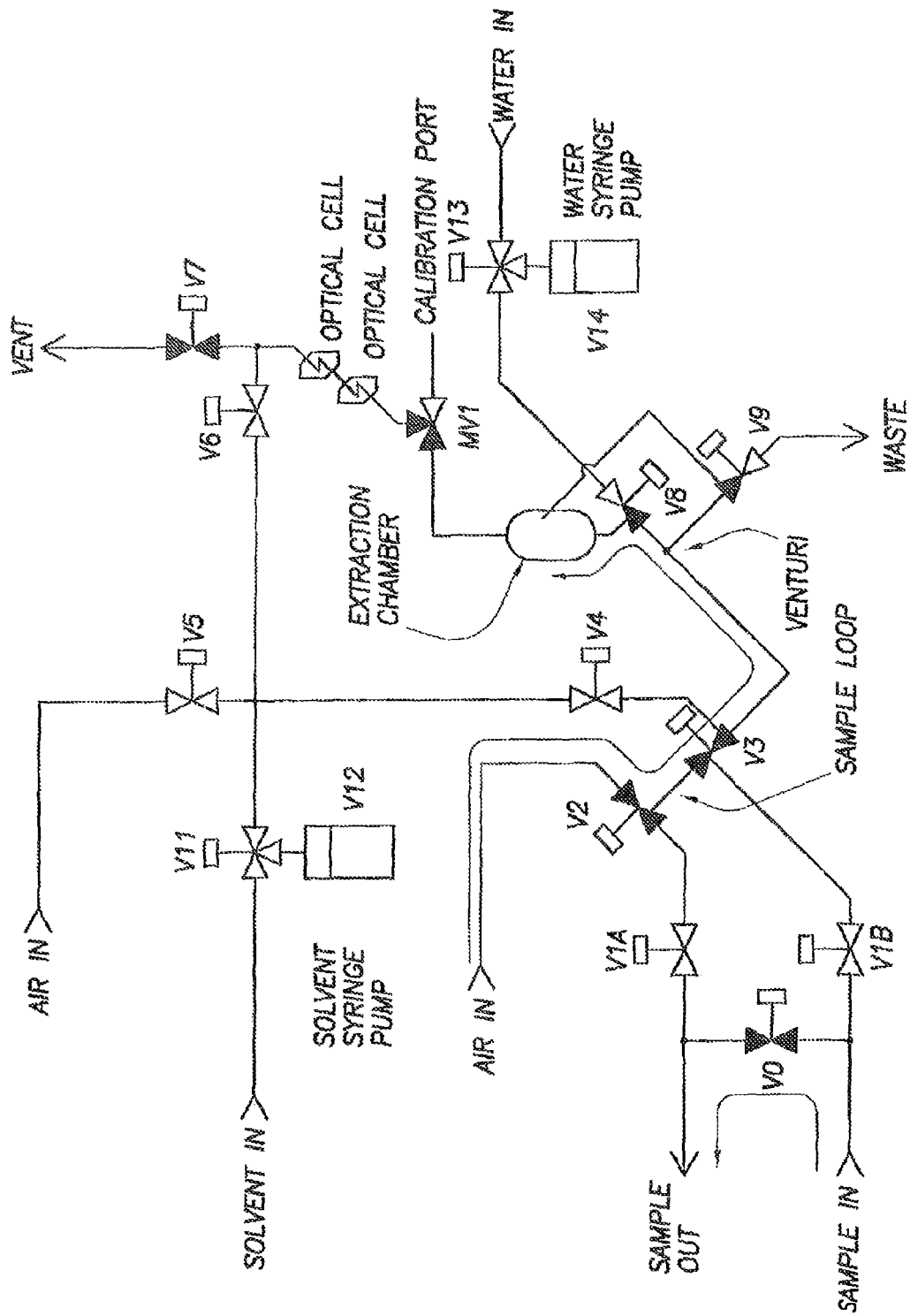
FIG. 2 depicts step 2 of how a sample is tested in the analyzer.

FIG. 2 depicts the effluent stream flowing through valve VO. From about 0.5 mL to about 50 ml of a sample are trapped between V3 and V2. Air pressure is used to blow the contents of the sample into extraction chamber via V2 and V3.

Figure 3:
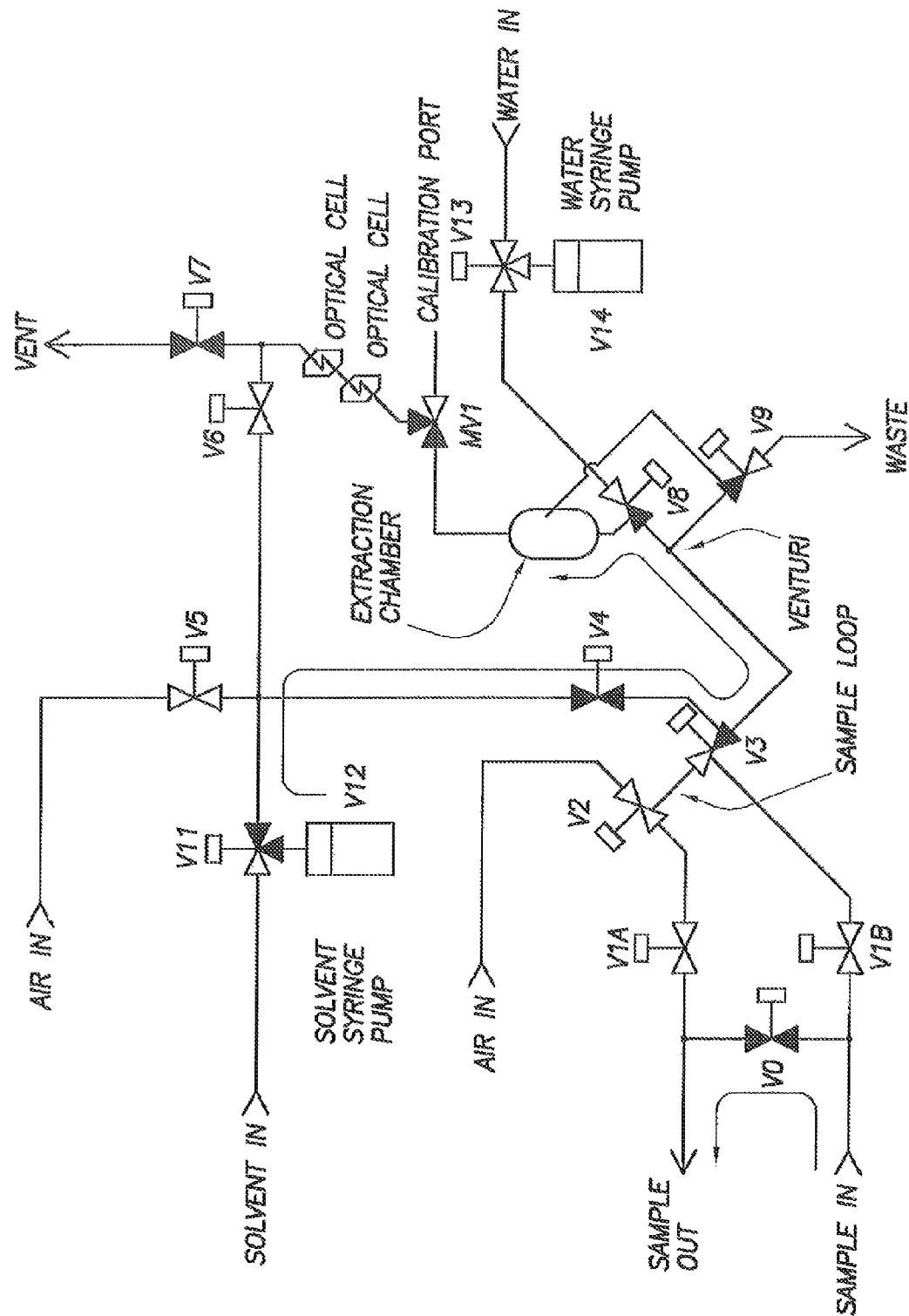
FIG. 3 depicts step 3 of how a sample is tested in the analyzer.

FIG. 3 depicts a pathway for the toluene to pick up any residual sample from the sample loop to the extraction chamber. It is in the extraction chamber where the sample and the known volume of toluene are mixed to create a hydrocarbon/solvent mixture.

Figure 4:
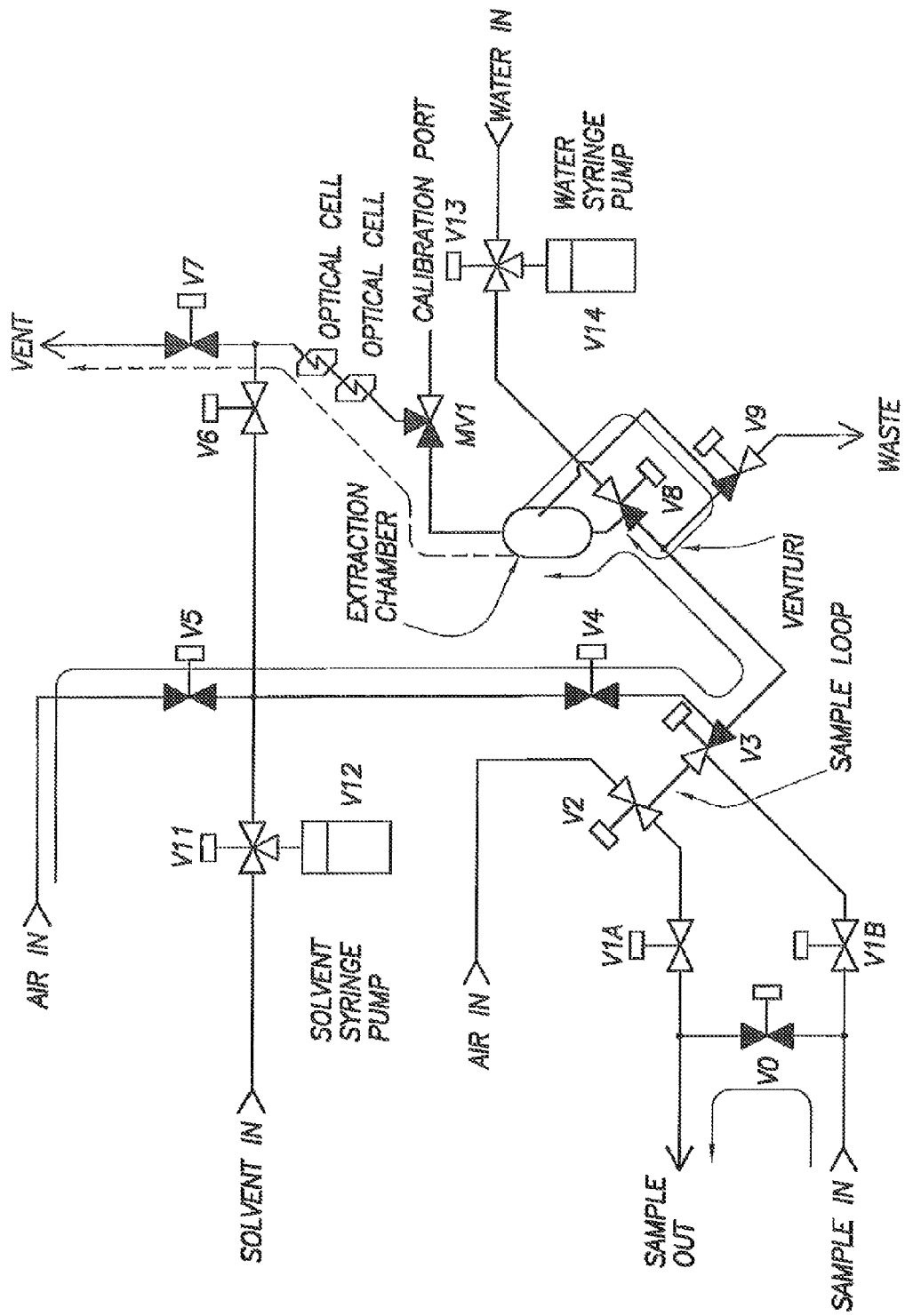
FIG. 4 depicts step 4 of how a sample is tested in the analyzer.

FIG. 4 depicts feeding air via V4 and V5 into the extraction chamber through the venturi to create pumping action, thereby pulling the toluene from the top of the extraction chamber. Excess air is routed through V7 to vent.

Figure 5:
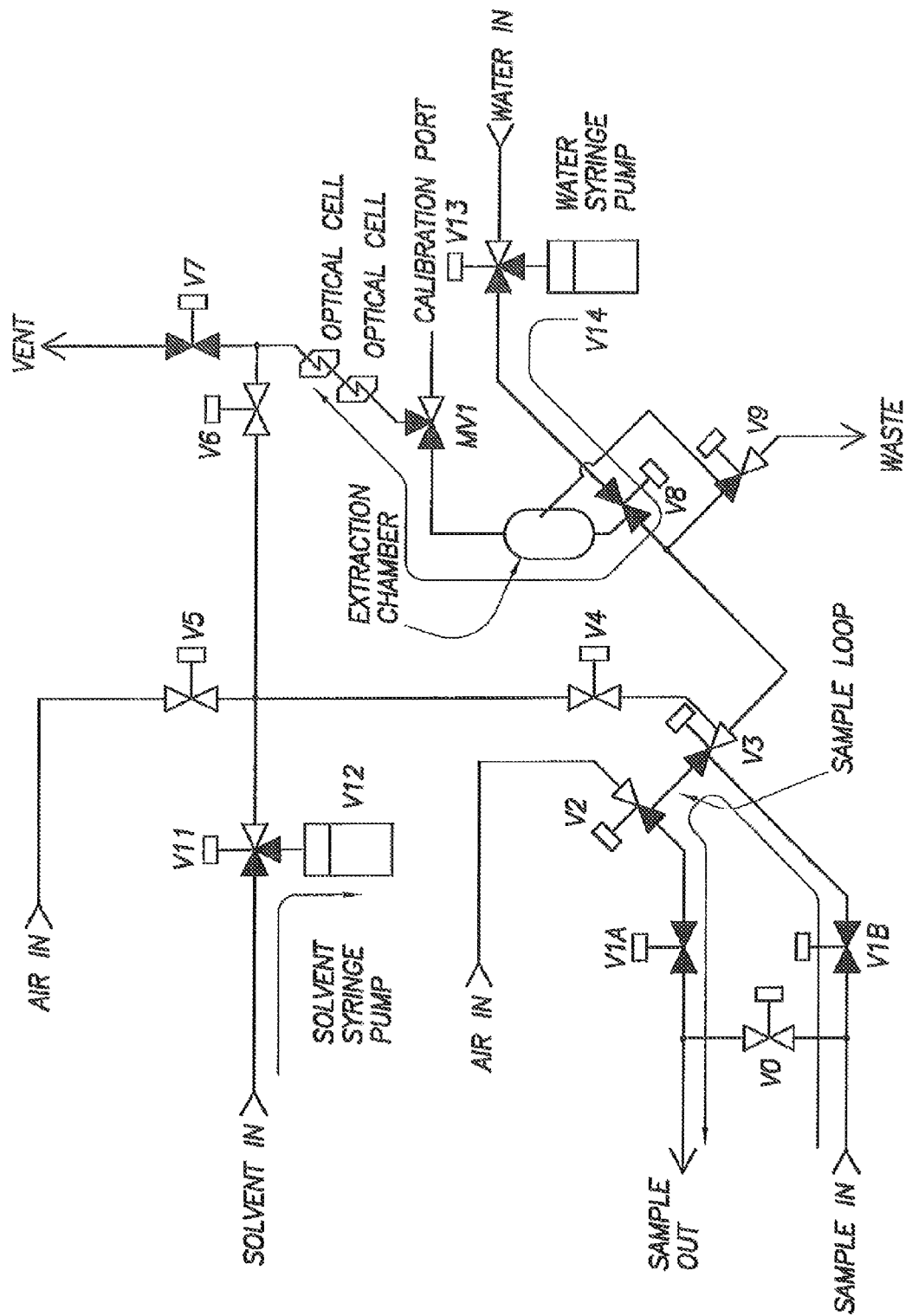
FIG. 5 depicts step 5 of how a sample is tested in the analyzer.
Figure 6:
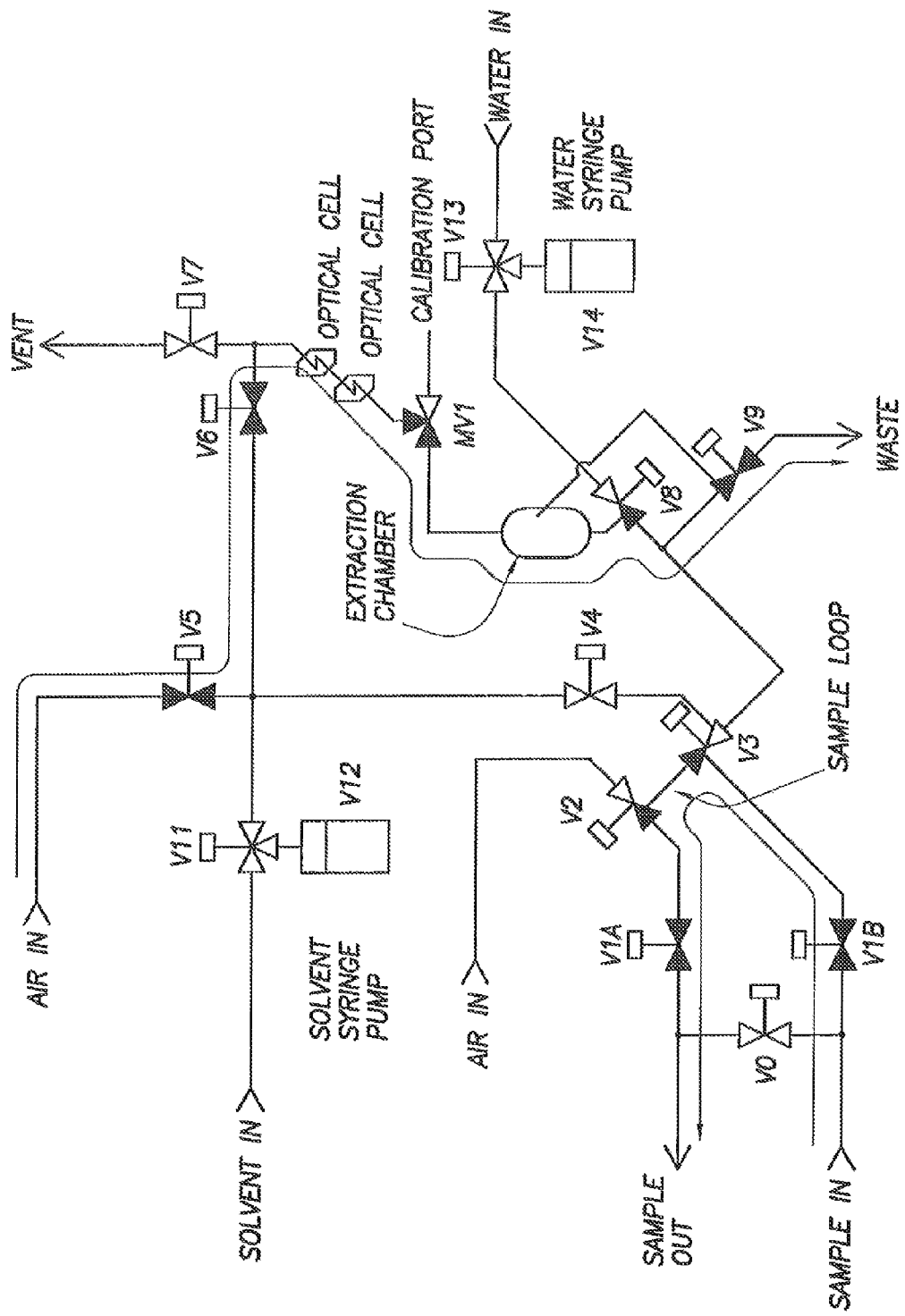
FIG. 6 depicts step 6 of how a sample is tested in the analyzer.

FIG. 5 depicts the reloading of the toluene syringe pump. Additionally water is injected from syringe pump via V8 and V13 into the bottom of the extraction chamber to lift, the hydrocarbon solvent mixture to a spectroscopic cell. FIG. 6 depicts transferring the leftover hydrocarbon/solvent mixture and water to a waste removal port.

Figure 7:
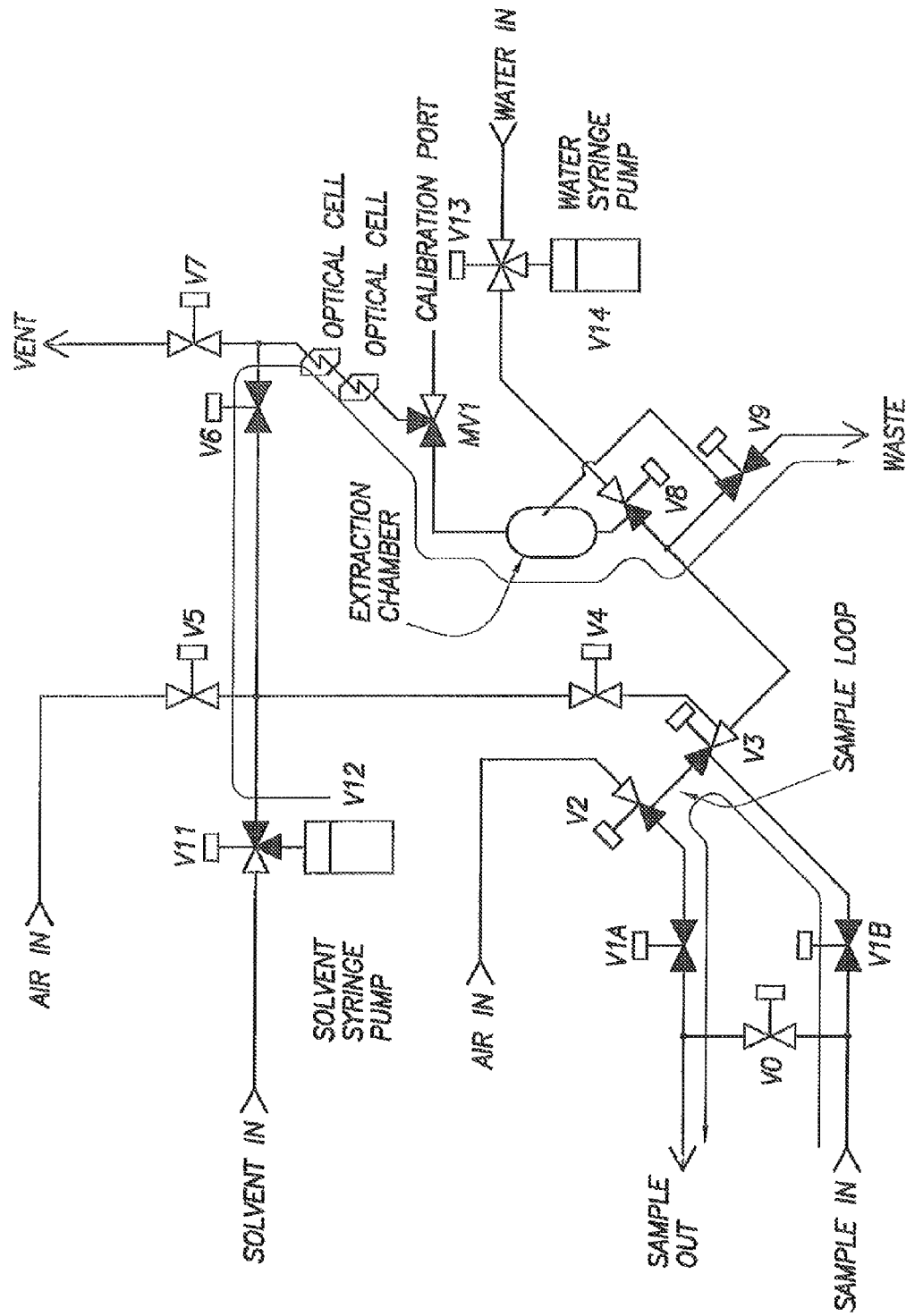
FIG. 7 depicts step 7 of how a sample is tested in the analyzer.

FIG. 7 depicts injecting toluene through valves V11 and V6 to solvent rinse the optical cells.

Figure 8:
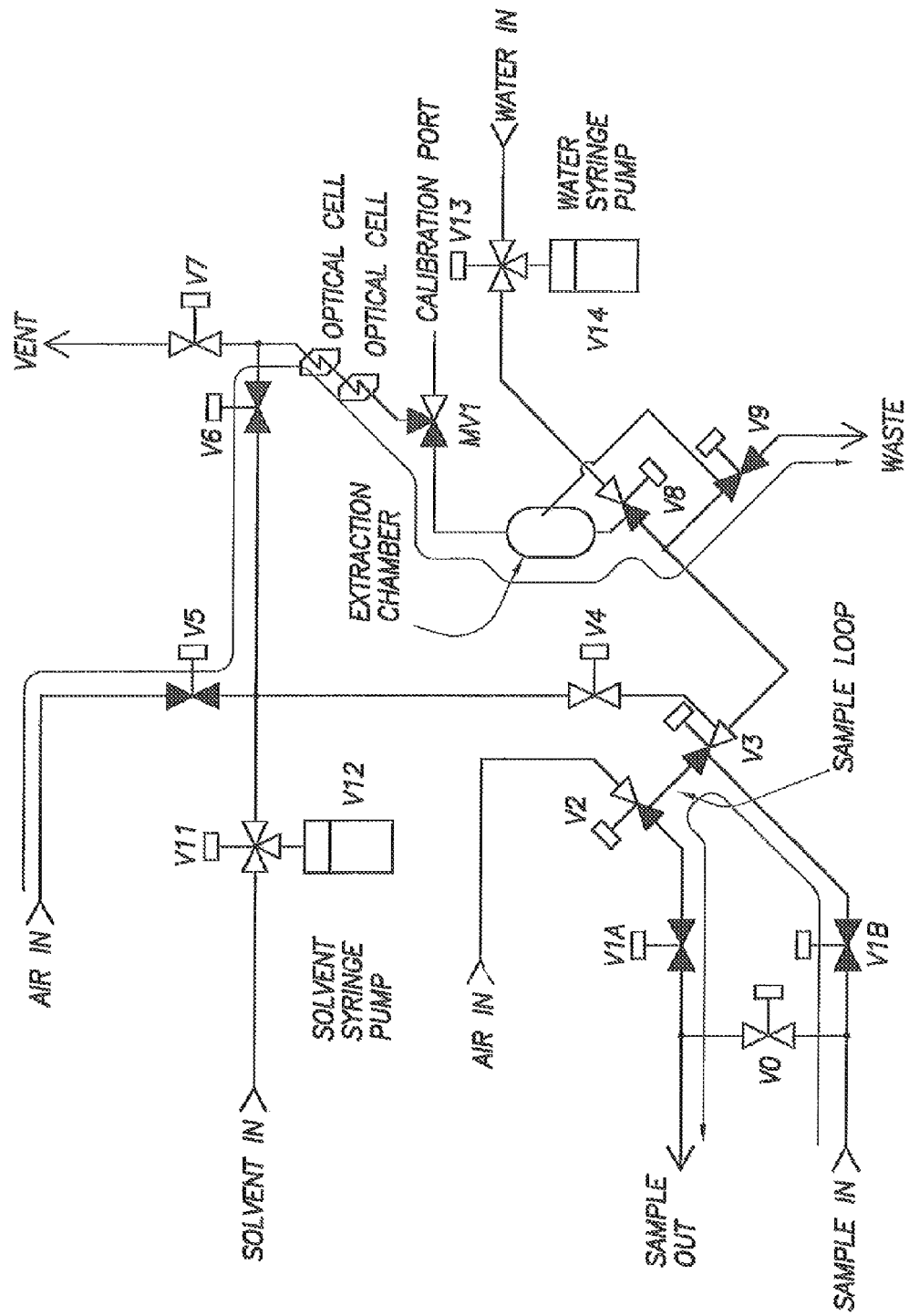
FIG. 8 depicts step 8 of how a sample is tested in the analyzer.

FIG. 8 depicts injecting air through valves V5, V6 and V9 to clear and evaporate rinsing solvent from the analyzer.

In one embodiment the operation can be set to a cycle as short as 7 minutes. The cycles may be run consecutively or with delay depending on the application need and solvent availability.

In one embodiment the method is completely automated. It only requires replenishment of solvent provided pressurized gas and water are obtained from operations. Data can be automatically transferred to a distributive control system (DCS), plant historian, or other database. Data can also be stored in onboard memory.

Figure 9:
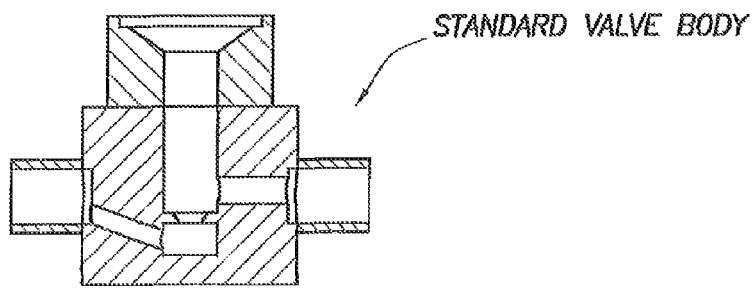
FIG. 9 depicts an embodiment of a first modified valve.
Figure 9:
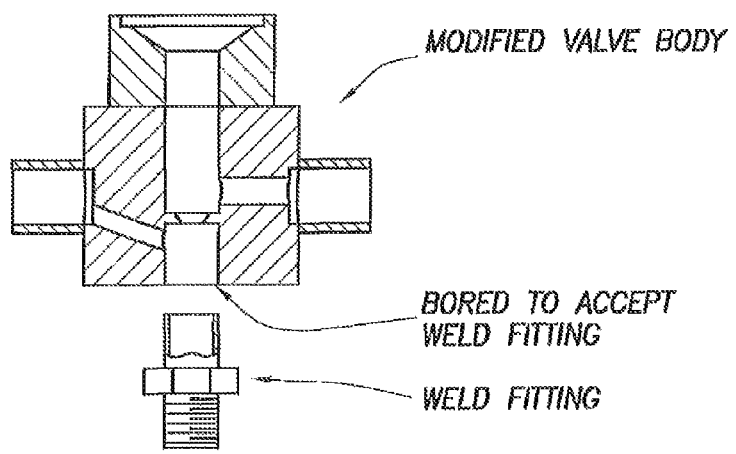
Figure 9:
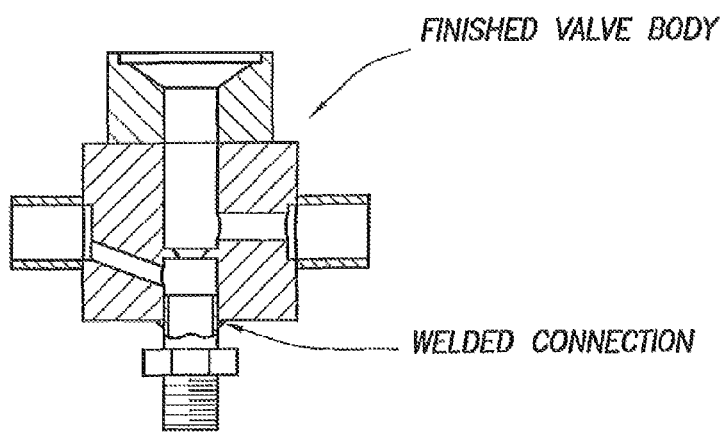

In another embodiment of the method the oil in water analyzer uses modified. valves. The first modified valve is shown in FIG. 9 wherein the modification would permit the sample stream to be routed through the body of the valve, keeping the valve internal component clear.

Figure 10:
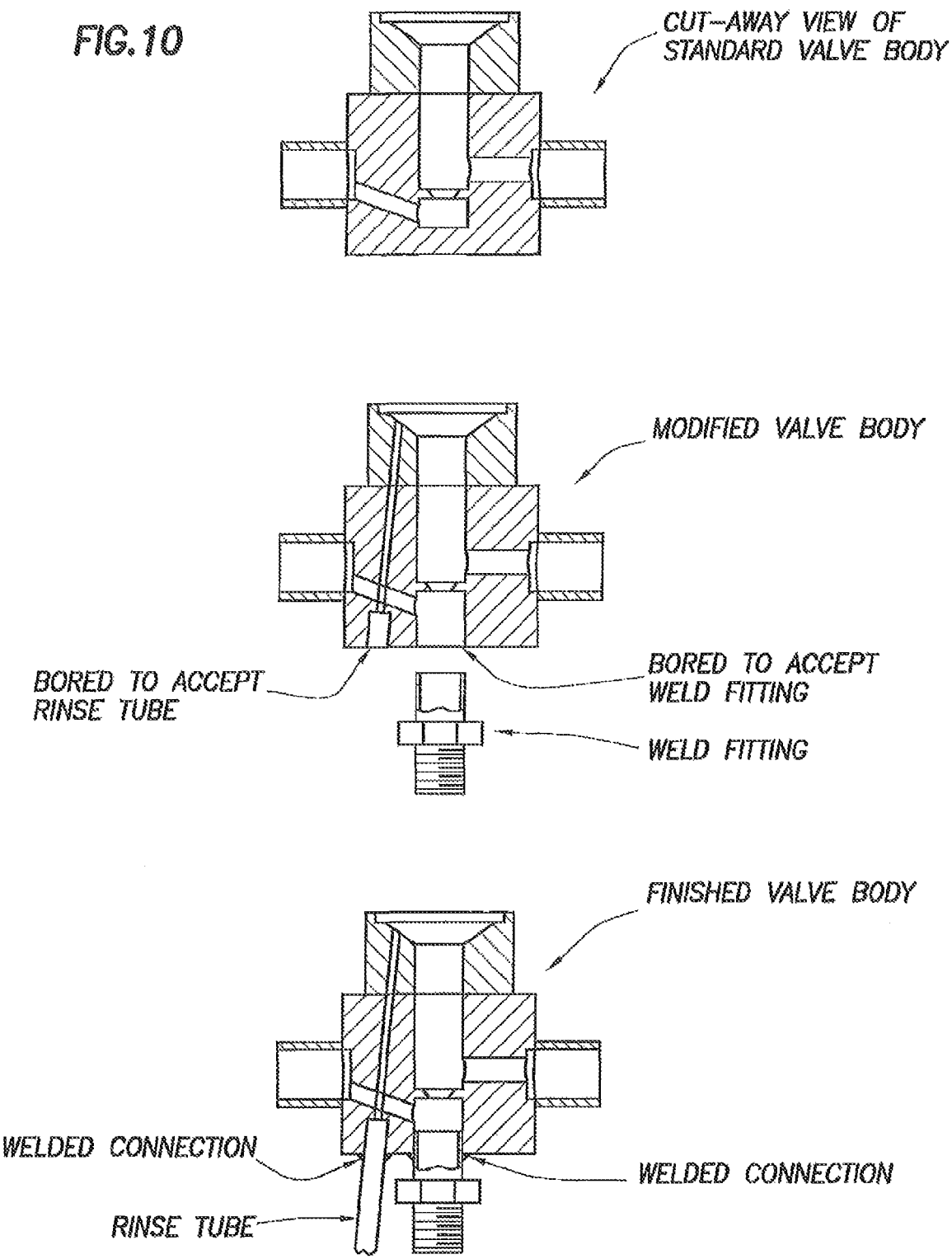
FIG. 10 depicts an embodiment of a second modified valve.

The second modified valve is be shown in FIG. 10 wherein a stainless steel tube is connected to the valve and provides a path to perform a solvent rinse of the downstream side of the valve body and the oil in water analyzer. In this embodiment the stainless steel tube is ⅛ inch in diameter.

The modified valves can be placed throughout the oil in water analyzer as needed.

Accordingly, the scope of protection is not limited by the description set out above, but is only limited by the claims which follow, that scope including all equivalents of the subject matter of the claims. Each and ever claim is incorporated into the specification as an embodiment of the present invention. Thus the claims are a further description and are an addition to the preferred embodiments of the present invention. The discussion of any reference is not an admission that it is prior art to the present invention, especially any reference that may have a publication date after the priority date of this application.

The invention claimed is:

1. An automated oil in water analyzer for analyzing the oil concentration in an effluent stream, the oil in water analyzer comprising:
    a dewatering/desalting system associated with the effluent stream;
    a sample loop connected to an effluent stream and arranged for acquiring a sample from the effluent stream, wherein the sample loop includes valving that may be opened to acquire a sample and closed to isolate the acquired sample from the effluent stream;
    an extraction device;
    valving for connecting the sample loop to the extraction device such that an acquired sample may be transferred into the extraction device;
    a pressurized gas system arranged to assist in the transfer of an acquired sample into the extraction device for extracting a hydrocarbon/solvent mixture from the sample;
    a solvent pump connected to the extraction device and suited for injecting a known volume of solvent into the extraction device to be mixed with the acquired sample;
    a spectroscopic cell for determining the hydrocarbon concentration of the hydrocarbon/solvent mixture by spectroscopy techniques;
    a water pump system for lifting the mixture of solvent and the acquired sample in the extraction device and transporting the same to the spectroscopic cell;
    a waste line arranged for discharging a fully analyzed mixture of an acquired sample and solvent; and
    a control system connected to the dewatering/desalting system and arranged to continuously alter operation of the dewatering/desalting system based upon the concentration of the hydrocarbon material in a sample.

2. The automated oil in water analyzer of claim 1 wherein the pressurized gas system is a pressurized air system.

* * * * *